(12) United States Patent
Chong (10) Patent No.: US 10,677,580 B2
(45) Date of Patent: Jun. 9, 2020

(54) OPTICAL COHERENCE TOMOGRAPHY SYSTEM USING POLARIZATION SWITCHING

(71) Applicant: SANTEC CORPORATION, Komaki, Aichi (JP)

(72) Inventor: Changho Chong, Los Altos, CA (US)

(73) Assignee: SANTEC CORPORATION, Komaki (JP)

( * ) Notice: Subject to any disclaimer, the term of this patent is extended or adjusted under 35 U.S.C. 154(b) by 412 days.

(21) Appl. No.: 15/139,579

(22) Filed: Apr. 27, 2016

(65) Prior Publication Data
US 2017/0314908 A1    Nov. 2, 2017

(51) Int. Cl.
*A61B 3/14* (2006.01)
*A61B 3/10* (2006.01)
(Continued)

(52) U.S. Cl.
CPC ........ *G01B 9/02011* (2013.01); *A61B 3/0025* (2013.01); *A61B 3/102* (2013.01);
(Continued)

(58) Field of Classification Search
CPC ....... A61B 3/102; A61B 5/0066; A61B 18/20; A61B 2017/00057; A61B 2018/00642;
(Continued)

(56) References Cited

U.S. PATENT DOCUMENTS 4,466,699 A   8/1984   Droessler et al.
5,022,745 A   6/1991   Zayhowski et al.
(Continued)

FOREIGN PATENT DOCUMENTS

DE   10 2011 114 797 A1   4/2013
JP       2006-202543 A    8/2006
(Continued)

OTHER PUBLICATIONS

Nankivil et al., "Handheld, rapidly switchable, anterior/posterior segment swept source optical coherence tomography probe," OSA Nov. 1, 2015; vol. 6, No. 11; DOI:10.1364/BOE.6.004516; Biomedical Optics Express 4516-4528.
(Continued)

*Primary Examiner* — Brandi N Thomas
(74) *Attorney, Agent, or Firm* — Foley & Lardner LLP (57) ABSTRACT

Optical coherence tomography (OCT) systems using a polarization switch and/or a polarization beam splitter are generally described. In an example, an OCT system includes a light source configured to emit a beam and an interferometer configured to receive the beam. The interferometer includes a reference path and an interferometer sample path. The OCT system further includes a polarization switch configured to selectively change a polarization state of the beam and a lens system that includes a first sample path and a second sample path. The polarization switch is further configured to direct the beam onto the first sample path upon selection of a first polarization state and to direct the beam onto the second sample path upon selection of a second polarization state that is different from the first polarization state.

18 Claims, 4 Drawing Sheets

(51) Int. Cl.
  *G01B 9/02* (2006.01)
  *A61B 3/117* (2006.01)
  *A61B 3/12* (2006.01)
  *G02B 27/28* (2006.01)
  *A61B 3/00* (2006.01)

(52) U.S. Cl.
  CPC .............. *A61B 3/117* (2013.01); *A61B 3/12* (2013.01); *G01B 9/02091* (2013.01); *G02B 27/283* (2013.01); *G01B 2290/70* (2013.01)

(58) Field of Classification Search
  CPC ....... A61B 3/0025; A61B 5/0075; A61B 3/10; A61B 3/1025; A61B 3/107; A61B 3/14; A61B 5/0086; A61B 3/0041; A61B 3/1233; A61B 5/0084; A61B 5/0261; A61B 5/444; A61B 3/113
  USPC ........ 351/200, 205, 206, 209–211, 221, 222, 351/243–246
  See application file for complete search history.

(56) References Cited

U.S. PATENT DOCUMENTS

| | | | |
|---|---|---|---|
| 5,319,668 A | 6/1994 | Luecke |
| 5,372,135 A | 12/1994 | Mendelson et al. |
| 5,430,574 A | 7/1995 | Tehrani |
| 5,491,524 A | 2/1996 | Hellmuth et al. |
| 5,537,162 A | 7/1996 | Hellmuth et al. |
| 5,561,523 A | 10/1996 | Blomberg et al. |
| 5,979,760 A | 11/1999 | Freyman et al. |
| 5,982,963 A | 11/1999 | Feng et al. |
| 6,070,093 A | 5/2000 | Oosta et al. |
| 6,111,645 A | 8/2000 | Tearney et al. |
| 6,134,003 A | 10/2000 | Tearney et al. |
| 6,160,826 A | 12/2000 | Swanson et al. |
| 6,275,718 B1 | 8/2001 | Lempert |
| 6,282,011 B1 | 8/2001 | Tearney et al. |
| 6,373,632 B1 | 4/2002 | Flanders |
| 6,421,164 B2 | 7/2002 | Tearney et al. |
| 6,485,413 B1 | 11/2002 | Boppart et al. |
| 6,501,551 B1 | 12/2002 | Tearney et al. |
| 6,556,853 B1 | 4/2003 | Cabib et al. |
| 6,564,087 B1 | 5/2003 | Pitris et al. |
| 6,725,073 B1 | 4/2004 | Motamedi et al. |
| 7,099,358 B1 | 8/2006 | Chong |
| 7,231,243 B2 | 6/2007 | Tearney et al. |
| 7,323,680 B2 | 1/2008 | Chong |
| 7,324,214 B2 | 1/2008 | De Groot et al. |
| 7,352,783 B2 | 4/2008 | Chong |
| 7,382,809 B2 | 6/2008 | Chong et al. |
| 7,388,891 B2 | 6/2008 | Uehara et al. |
| 7,400,410 B2 | 7/2008 | Baker et al. |
| 7,414,779 B2 | 8/2008 | Huber et al. |
| 7,428,057 B2 | 9/2008 | De Lega et al. |
| 7,489,713 B2 | 2/2009 | Chong et al. |
| 7,701,588 B2 | 4/2010 | Chong |
| 7,725,169 B2 | 5/2010 | Boppart et al. |
| 7,835,010 B2 | 11/2010 | Morosawa et al. |
| 7,865,231 B2 | 1/2011 | Tearney et al. |
| 7,869,057 B2 | 1/2011 | De Groot |
| 7,884,945 B2 | 2/2011 | Srinivasan et al. |
| 7,961,312 B2 | 6/2011 | Lipson et al. |
| 8,036,727 B2 | 10/2011 | Schurman et al. |
| 8,115,934 B2 | 2/2012 | Boppart et al. |
| 8,315,282 B2 | 11/2012 | Huber et al. |
| 8,405,834 B2 | 3/2013 | Srinivasan et al. |
| 8,427,649 B2 | 4/2013 | Hays |
| 8,500,279 B2 | 8/2013 | Everett et al. |
| 8,625,104 B2 | 1/2014 | Izatt et al. |
| 8,690,328 B1 | 4/2014 | Chong |
| 8,690,330 B2 | 4/2014 | Hacker et al. |
| 9,163,930 B2 | 10/2015 | Buckland et al. |
| 9,335,154 B2 | 5/2016 | Wax et al. |
| 9,851,433 B2 | 12/2017 | Sebastian |
| 2001/0034478 A1 | 10/2001 | Lambert et al. |
| 2002/0163948 A1 | 11/2002 | Yoshida et al. |
| 2004/0036838 A1 | 2/2004 | Podoleanu et al. |
| 2004/0257581 A1 | 12/2004 | Hogan |
| 2005/0171438 A1 | 8/2005 | Chen et al. |
| 2005/0201432 A1 | 9/2005 | Uehara et al. |
| 2005/0213103 A1 | 9/2005 | Everett et al. |
| 2006/0105209 A1 | 5/2006 | Thyroff et al. |
| 2006/0109872 A1 | 5/2006 | Sanders |
| 2006/0215713 A1 | 9/2006 | Flanders et al. |
| 2007/0040033 A1 | 2/2007 | Rosenberg |
| 2007/0076217 A1 | 4/2007 | Baker et al. |
| 2007/0081166 A1 | 4/2007 | Brown et al. |
| 2007/0133647 A1 | 6/2007 | Daiber |
| 2007/0141418 A1 | 6/2007 | Ota et al. |
| 2007/0263226 A1 | 11/2007 | Kurtz et al. |
| 2007/0291277 A1 | 12/2007 | Everett et al. |
| 2008/0097194 A1 | 4/2008 | Milner |
| 2008/0269575 A1 | 10/2008 | Iddan |
| 2009/0022181 A1 | 1/2009 | Atkins et al. |
| 2009/0079993 A1 | 3/2009 | Yatagai et al. |
| 2009/0103050 A1 | 4/2009 | Michaels et al. |
| 2009/0169928 A1 | 7/2009 | Nishimura et al. |
| 2009/0247853 A1 | 10/2009 | Debreczeny |
| 2009/0268020 A1 | 10/2009 | Buckland et al. |
| 2009/0290613 A1 | 11/2009 | Zheng et al. |
| 2010/0110171 A1 | 5/2010 | Satake |
| 2010/0157308 A1 | 6/2010 | Xie |
| 2010/0246612 A1 | 9/2010 | Shimizu |
| 2010/0253908 A1 | 10/2010 | Hammer et al. |
| 2010/0284021 A1 | 11/2010 | Hacker |
| 2011/0112385 A1 | 5/2011 | Aalders |
| 2011/0228218 A1 | 9/2011 | Hauger et al. |
| 2011/0235045 A1 | 9/2011 | Koerner |
| 2011/0255054 A1 | 10/2011 | Hacker et al. |
| 2011/0299034 A1 | 12/2011 | Walsh et al. |
| 2012/0013849 A1 | 1/2012 | Podoleanu et al. |
| 2012/0026466 A1 | 2/2012 | Zhou et al. |
| 2012/0133950 A1 | 5/2012 | Suehira et al. |
| 2012/0136259 A1 | 5/2012 | Milner et al. |
| 2012/0188555 A1* | 7/2012 | Izatt ..................... A61B 3/102 356/479 |
| 2013/0265545 A1 | 10/2013 | Buckland et al. |
| 2014/0051952 A1 | 2/2014 | Reichgott et al. |
| 2014/0055749 A1 | 2/2014 | Zhou et al. |
| 2014/0111774 A1 | 4/2014 | Komine |
| 2014/0228681 A1 | 8/2014 | Jia et al. |
| 2014/0268163 A1 | 9/2014 | Milner et al. |
| 2014/0293290 A1 | 10/2014 | Kulkarni |
| 2014/0336479 A1 | 11/2014 | Ando |
| 2015/0223681 A1* | 8/2015 | Kuranov ............ G01B 9/02004 600/425 |
| 2015/0342508 A1 | 12/2015 | Chong |
| 2015/0348287 A1 | 12/2015 | Yi et al. |
| 2016/0178346 A1 | 6/2016 | Kulkarni |
| 2016/0324593 A1 | 11/2016 | El-Haddad et al. |
| 2017/0090031 A1 | 3/2017 | Bondy et al. |
| 2018/0088236 A1 | 3/2018 | Eichenholz et al. |
| 2018/0128594 A1 | 5/2018 | Lee et al. |

FOREIGN PATENT DOCUMENTS

| | | |
|---|---|---|
| JP | 2008-188047 | 8/2008 |
| JP | 2010-172538 | 8/2010 |
| WO | WO-2012/075126 A2 | 6/2012 |
| WO | WO-2013/168149 A1 | 11/2013 |
| WO | WO-2015/121756 A2 | 8/2015 |
| WO | WO-2017/176901 A1 | 10/2017 |

OTHER PUBLICATIONS

Changho Chong, et al. "Large Coherence Length Swept Source for Axial Length Measurement of the Eye." Applied Optics 48:10 (2009): D145-150.

Chowdhury, Md Koushik et al., Challenges & Countermeasures in Optical Noninvasive Blood Glucose Detection, International Journal of Innovative Research in Science, Engineering and Technology vol. 2, Issue 1, Jan. 2013 (6 pages).

(56) References Cited

OTHER PUBLICATIONS

Dai et al., "Optical coherence tomography for whole eye segment imaging," Optics Express, vol. 20, No. 6 (2012) pp. 6109-6115.
Dhalla, et al., "Simultaneous swept source optical coherence tomography of the anterior segment and retina using coherence revival," Optics Letters, 2012, vol. 37, No. 11, pp. 1883-1885.
English Translation of the International Search Report and Written Opinion on International Application No. PCT/EP2009/009189, dated Apr. 6, 2010, 12 pages.
F. Lexer et al., "Wavelength-tuning interferometry of intraocular distances," Applied Optics, vol. 36, No. 25, pp. 6548-6553 (Sep. 1, 1997).
Fainman, Y. et al., "Nanophotonics for Information Systems," Information Optics and Photonics (T. Fournel and B. Javidi eds., Springer New York, 2010) pp. 13-37.
International Preliminary Report on Patentability and Written Opinion on International Application No. PCT/US2015/032727 dated Dec. 8, 2016(7 pages).
International Preliminary Report on Patentability in corresponding application PCT/US2016/035012 dated Dec. 14, 2017.
International Preliminary Report on Patentability in corresponding international application No. PCT/US2015/019299 dated Sep. 22, 2016.
International Preliminary Report on Patentability in corresponding international application No. PCT/US2015/032727 dated Dec. 8, 2016.
International Preliminary Report on Patentability in International appln. No. PCT/IB2015/000808.
International Search Report and Written Opinion dated Aug. 26, 2015 for PCT/US15/32727 (8 pages).
International Search Report and Written Opinion in corresponding application No. PCT/US2016/035012 dated Aug. 18, 2016.
International Search Report and Written Opinion in International Application No. PCT/US2015/19299 dated Nov. 2, 2015 (10 pages).
International Search Report and Written Opinion in PCT/IB2015/000808 dated Oct. 20, 2015 (12 pages).
Jeong, et al., "Spectral-domain OCT with dual illumination and interlaced detection for simultaneous anterior segment and retina imaging," Optics Express, 2012, vol. 20, Issue 17, pp. 19148-19159.
Jia et al., Split-Spectrum Amplitude-Decorrelation Angiography with Optical Coherence Tomography, Optics Express, vol. 20 No. 4, Feb. 9, 2012, pp. 4710-4725.
Lexer et al., "Wavelength-tuning interferometry of intraocular distances", Applied Optics, vol. 36, No. 25, Sep. 1, 1997, pp. 6548-6553.
Mariampillai et al., Speckle Variance Detection of Microvasculature Using Swept-Source Optical Coherence Tomography, Optics Letters, vol. 33 No. 13, Jul. 1, 2008, pp. 1530-1532.
Non-Final Rejection on U.S. Appl. No. 14/723,325 dated Dec. 7, 2017.
P. Tayebati et al., "Microelectromechanical tunable filter with stable half symmetric cavity," Electronics Letters, vol. 34, No. 20, pp. 1967-1968 (Oct. 1, 1998).
Poddar, et al., "Non-Invasive Glucose Monitoring Techniques: A Review and Current Trends," Oct. 31, 2008, pp. 1-47.
Sarlet, G. et al., "Wavelength and Mode Stabilization of Widely Tunable SG-DBR and SSG-DBR Lasers," IEEE Photonics Technology Letters, vol. 11, No. 11, Nov. 1999, pp. 1351-1353.
Segawa, Toru et al., "Semiconductor Double-Ring-Resonator-Coupled Tunable Laser for Wavelength Routing," IEEE Journal of Quantum Electronics, vol. 45, No. 7, Jul. 2009, pp. 892-899.
Sergie Ortiz, et al. "Corneal Topography From Spectral Optical Coherence Tomography (SOCT)." Biomedical Optics Express 2:12, (2011):3232-3247.
U.S. Notice of Allowance on 105093-0102 dated Dec. 6, 2013.
U.S. Notice of Allowance on U.S. Appl. No. 14/601,945 dated Sep. 13, 2016.
U.S. Notice of Allowance on U.S. Appl. No. 14/613,644 dated Nov. 7, 2016.
U.S. Notice of Allowance on U.S. Appl. No. 14/613,644 dated Nov. 18, 2016.
U.S. Notice of Allowance on U.S. Appl. No. 14/641,200 dated Jul. 12, 2016.
U.S. Office Action on 105093-0102 dated Sep. 12, 2013.
U.S. Office Action on 105093-0116 dated Aug. 19, 2015.
U.S. Office Action on U.S. Appl. No. 14/601,945 dated Mar. 2, 2016.
U.S. Office Action on U.S. Appl. No. 14/613,644 dated Jun. 8, 2016.
U.S. Office Action on U.S. Appl. No. 14/641,200 dated Mar. 14, 2016.
U.S. Office Action on U.S. Appl. No. 14/641,200 dated Dec. 7, 2015.
U.S. Office Action on U.S. Appl. No. 14/723,325 dated Nov. 18, 2016.
U.S. Office Action on U.S. Appl. No. 14/723,325 dated Apr. 24, 2017.
U.S. Office Action on U.S. Appl. No. 15/202,925 dated Jul. 27, 2017.
Chopra et al., Topographical Thickness of the Skin in the Human Face, Aesthetic Surgery Journal, vol. 35(8), 2015, pp. 1007-1013.
International Search Report and Written Opinion in International Application PCT/US2019/027671 dated Jul. 1, 2019.
Poddar, et al., "Non-Invasive Glucose Monitoring Techniques: A Review and Current Trends," Oct. 2008, pp. 1-47.

* cited by examiner

OPTICAL COHERENCE TOMOGRAPHY SYSTEM USING POLARIZATION SWITCHING

BACKGROUND

The following description is provided to assist the understanding of the reader. None of the information provided or references cited is admitted to be prior art.

Optical coherence tomography (OCT) is an imaging technique. OCT imaging techniques are often used in a medical setting. The techniques are capable of producing three dimensional images from within optical scattering samples, such as biological tissue. In other words, light scattered by a sample can be detected in order to form an image of the sample. When imaging a sample, parts of the sample below its surface can be imaged. Examples of biological tissue that may be imaged using OCT include coronary arteries, skin, and an eye. In another example, OCT may be used for art conservation to analyze layers of a painting.

OCT is often accomplished with the use of an interferometer. An interferometer utilizes light that is reflected back from a sample and a reference light. The reference light is generally configured to travel a similar distance as light that is reflected back from the sample. The light from the sample and the reference light can be combined in such a way that gives rise to an interference pattern. That is, the light from the sample and the reference light will either constructively or destructively interfere with each other. The level of interference that occurs indicates the reflectivity of areas of the sample, such that structures within the sample may be identified and imaged.

SUMMARY

In an embodiment, the present technology provides an improved optical coherence tomography (OCT) system using polarization switching to enable simultaneous imaging of different portions of a sample, for example, for imaging the anterior chamber and retina of an eye. In one embodiment, an OCT system includes a light source configured to emit a beam and an interferometer configured to receive the beam. The interferometer includes a reference path and an interferometer sample path. The OCT system further includes a polarization switch configured to selectively change a polarization state of the beam and a lens system that includes a first sample path and a second sample path. The polarization switch is further configured to direct the beam onto the first sample path upon selection of a first polarization state and to direct the beam onto the second sample path upon selection of a second polarization state that is different from the first polarization state.

In another illustrative embodiment, the OCT system includes a light source configured to emit a beam and an interferometer configured to receive the beam. The interferometer includes a reference path and an interferometer sample path. The OCT system further includes a polarization beam splitter configured to divide the beam into a first sample path and a second sample path and a lens system that includes the first sample path and the second sample path. The first sample path and the second sample path are configured to direct a portion of the light on each respective path to a dump path.

An illustrative method includes emitting, by a light source, a first beam and directing the beam into an interferometer. The interferometer includes a reference path and an interferometer sample path. The method further includes selecting, by a polarization switch, a polarization state of the beam. The method also includes directing, by a lens system, the beam across one of a first sample path or a second sample path to a sample based on the polarization state of the beam, and imaging the sample.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Described herein is an improved optical coherence tomography (OCT) system that uses polarization switching to enable selection of different imaging depth ranges for imaging different portions of an eye, for example, for imaging both the anterior chamber and retina of an eye.

Imaging the anterior chamber of an eye utilizes a different optical configuration than imaging for the retina of an eye. For the anterior chamber of the eye, a beam scan may be generally perpendicular to the sample (or cornea) and the beam has a shallow focus. When imaging the retina, a beam can be refracted by the eye itself, so a beam scan may be convergent with a collimated larger beam size for deep focusing in the eye. In other words, a beam used to scan the retinal area of the eye must enter the eye at a different angle than a beam used to scan the anterior chamber of the eye. Advantageously, the system and methods disclosed herein can image both the anterior chamber and the retina of an eye by using a polarization switching mechanism to create multiple light paths suitable for imaging different respective depth ranges. These multiple light paths can be recombined into a single light path so that the system shares a same optical axis and aperture for different imaging depths (e.g., anterior chamber, retina, posterior chamber, entire eye, etc.) without losing sensitivity in each imaging zone.

Further, the methods and systems disclosed herein can utilize a single detector and interferometer to detect two imaging ranges. Previously, systems have utilized multiple interferometers and multiple photo-detectors in order to image two samples at once. The methods and systems disclosed herein use a single interferometer and photo-detector, greatly decreasing the cost, complexity, and size of an OCT system designed to scan multiple samples at once.

The methods and systems disclosed herein advantageously also achieve a small footprint and more stable scanning for the corresponding imaging device by keeping the optics stationary when scanning in multiple configurations. This is in contrast with traditional zooming or switching mechanisms that utilized complex mechanisms to adjust the focus and incidence angle of a single beam in order to realize multiple imaging ranges. Such traditional systems utilized complex switchable or adjustable lenses to adjust a single beam in order to switch between multiple imaging ranges. Such a configuration is complex, has many moving parts, and may be quite large. Further, such a configuration may not allow real time imaging of multiple imaging ranges. The methods and systems disclosed herein advantageously reduce the number of components utilized for multiple imaging ranges and allows for real time imaging of multiple imaging ranges. For example, the systems and methods disclosed herein can achieve real time imaging of two imaging ranges, such as an anterior chamber of an eye and the retinal area of an eye.

Various embodiments using polarization switching also achieve greater efficiency (e.g., less insertion loss) than traditional beam splitting approaches. Traditional beam splitting approaches (which split a beam into multiple paths) compromised sensitivity due to the loss of optical power in each path. For example, a beam split into two paths would exhibit only 50% (or less) power in each path. In contrast, embodiments described herein using polarization switches maximize the use of the source power and corresponding sensitivity for each imaging depth range because the beam is not split, but rather is switched onto different paths.

In addition, polarization switching embodiments eliminate strict coherence length requirements for the swept source that are needed for beam splitting approaches. Simultaneous imaging using a beam splitting approach typically requires a longer coherence length for the swept source to account for potential overlapping of the different imaging zones desired to be simultaneously imaged. Such longer coherence lengths are not required for the polarization switching approaches discussed below.

In an illustrative embodiment, a light source is configured to emit a beam of light. In one embodiment, a wavelength swept source may be utilized as the light source. The output of the light source is directed an interferometer. The interferometer creates a reference path and a sample path. The sample path is a path through which the beam is transmitted to be reflected off the sample (e.g., an eye). The reference path is a separate path through which the beam is reflected to have the same optical length as the sample path, such that the interferometer can generate an accurate image of the sample.

The beam of light is output from the interferometer, and a polarization switch switches the polarization state of the sample path between a first polarization state and a second polarization state that is orthogonal to the first polarization state. The switching of the polarization state causes the selection of a corresponding sample path, e.g., a first sample path or a second sample path. On a return path (when light from the sample paths is reflected or backscattered), the reflected light is returned to the interferometer on a common axis. In an embodiment, the first and second sample paths share a single common lens system.

One of the sample paths includes a lens configuration that enables a collimated beam configured for convergent scanning such that the system can scan the retinal area of the eye. In other words, this sample path has a lens system with a collimating beam and a convergent scanning pattern relative to the sample. The collimating beam is focused at the retinal area after passing through the eye lens system and can be scanned across the retinal area because of convergent scanning before entering the eye. Accordingly, the path length of the sample path that scans the retinal area will be longer than the path length of the sample path that scans the anterior chamber of the eye. The difference between the first sample path length and the second sample path length can be an optical length equivalent to the axial length of a human eye.

A second of the sample paths includes a lens configuration that enables a beam capable of scanning perpendicular to the anterior chamber position of the eye. In other words, this sample path has a lens system with a divergent beam and lateral scanning pattern that is perpendicular to the sample.

Figure 1:
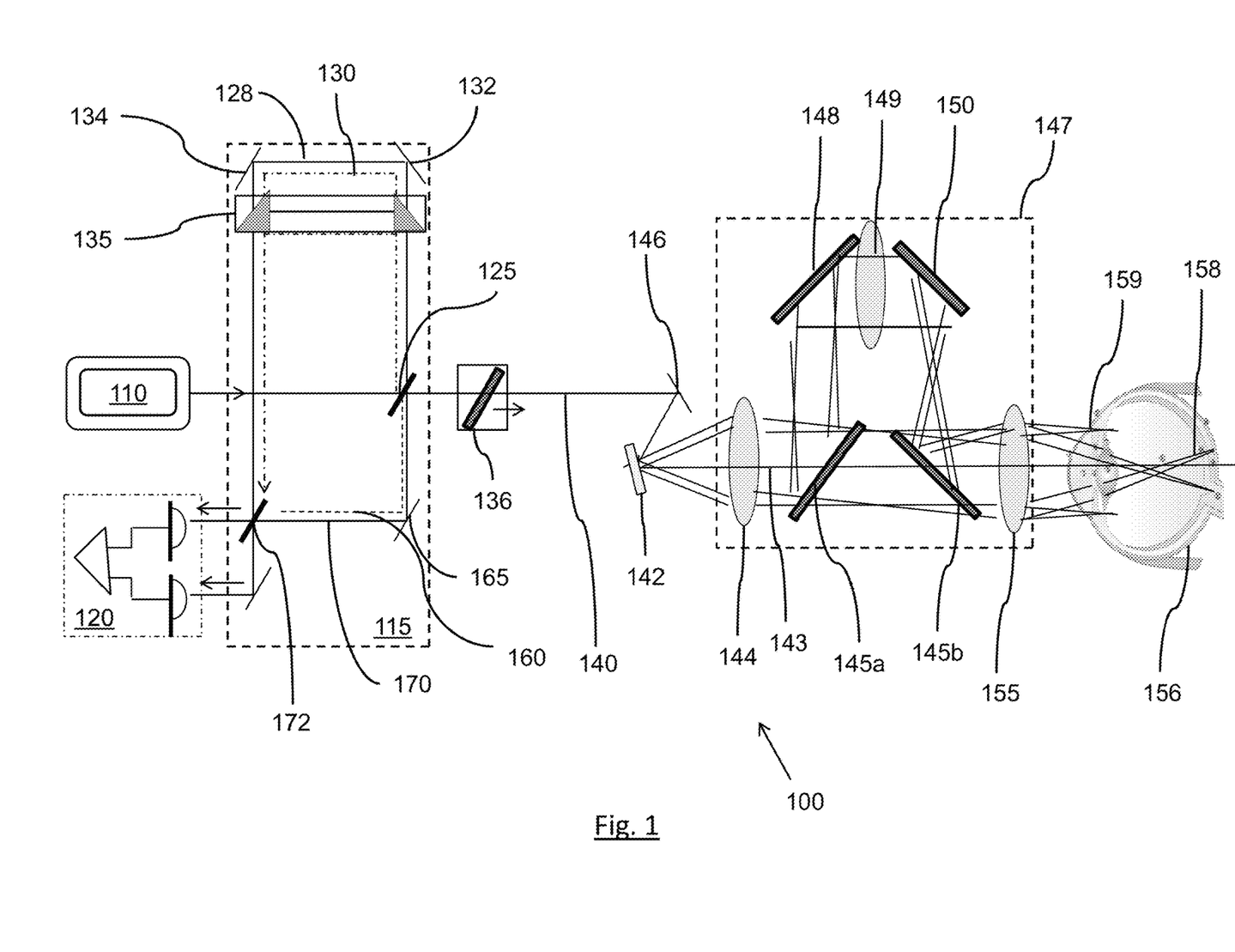
FIG. 1 depicts a representation of an optical coherence tomography (OCT) system using a polarization switch in accordance with an illustrative embodiment.

FIG. 1 depicts a representation of an optical coherence tomography (OCT) system 100 using a polarization switch in accordance with an illustrative embodiment. In alternative embodiments, fewer, additional, and/or different elements may be present. The OCT system 100 includes a light source 110 that emits a beam 140. The beam 140 is directed into an interferometer 115. The interferometer includes a reference path 128 and an interferometer sample path 170. The direction of the reference path 128 in accordance with an embodiment is shown by an arrow 130. The beam 140 from the light source 110 passes through the interferometer 115 to a mirror 125. The mirror 125 is a half-mirror that reflects some of the light that hits it, but allows other light to pass through. Accordingly, some of the beam 140 is reflected into the reference path 128. The reference path 128 includes two different paths that correspond with a first sample path length and a second sample path length of a lens system 147. That is, the reference path 128 is capable of changing depending on which part of the sample (e.g., an eye) is being imaged (and subsequently which sample path is being utilized to perform the imaging).

Accordingly, in an example embodiment, when a first sample path is being utilized with the beam 140 to measure an anterior segment of an eye 156, the reference path 128 is longer, and the light is reflected off of a mirror 132 and a mirror 134. When a second sample path is being utilized to measure a retinal area of the eye 156, a path length switch 135 is activated to shorten the reference path 128, which corresponds to the difference in path length between the first sample path and the second sample path. In an alternative embodiment, the reference path 128 (and the shortened reference path when the path length switch 135 is activated) may be variable in order to provide depth scanning of the eye 156. In an alternative embodiment, instead of having a path length switch 135, the difference in path length between a reference path corresponding to the first sample path and a reference corresponding to the second sample path may be pre-adjusted or predetermined in order to have relative offset/non-offset of depth ranges between the anterior chamber and retinal areas of the eye.

When the beam 140 is reflected back from the first sample, it is reflected by the mirror 125 into the interferometer sample path 170. The direction of the interferometer sample path 170 in an embodiment is indicated by an arrow 160. The light in the interferometer sample path is reflected by a mirror 165. At a mirror 172 (e.g., a half-mirror), the light from the reference path 128 and the interferometer sample path 170 are combined and are received by a balanced photo-detector 120, from which two images of the sample can be generated.

The portion of the beam 140 that passes through the mirror 125 is output from the interferometer 115 and passed to a polarization switch 136. In the embodiment of FIG. 1, the polarization switch 136 is a 1×1 switch that is configured to selectively change the polarization of the light from beam 140. In one embodiment, the polarization switch 136 configured to switch the polarization of the light from beam 140 between two or more orthogonal polarization states. In an embodiment, the polarization switch 136 may be a half-waveplate switch, a liquid crystal switch, or an electro-optics modulator. In additional embodiments, the polarization switch 136 may include any polarization switch known to those of skill in art capable of switching light between two or more orthogonal polarization states.

On the return path, when the beam 140 has been reflected or backscattered, the polarization switch 136 acts as an isolator to discriminate the cross-polarization with respect to the input polarization. For example, if the polarization switch 136 is placed in a first state that passes light having a first polarization state, the polarization switch 136 will pass reflected light on the return path that is in the first polarization state, while blocking light having an orthogonal polarization to the light in the first polarization state. Likewise, if the polarization switch 136 is placed in a second state that passes light having a second polarization state (that is orthogonal to the first polarization state), the polarization switch 136 will pass reflected light on the return path that is in the second polarization state, while blocking light having an orthogonal polarization to the light in the second polarization state (e.g., light in the first polarization state).

After passing through the polarization switch 136, beam 140 is reflected off of a mirror 146 and onto a scan mirror 142. The scan mirror 142 is configured to direct the beam 140 toward the lens system 147. The lens system 147 includes two different paths (i.e., a first sample path and a second sample path) corresponding to two different orthogonal polarization states. In other words, if the beam 140 has a first polarization state, it is passed through the first sample path, but if the beam 140 has a second polarization state that is orthogonal to the first polarization state the beam 140 is passed through the second sample path.

In an embodiment, the scan mirror 142 is configured to be at a focal point of a lens 144. The lens 144 and a lens 155, in this embodiment, are configured to be in a 4*f* configuration. The beam 140 passes through the lens 144 a polarization beam splitter 145*a*. Depending on the polarization state of the beam 140 as determined by the polarization switch 136, the polarization beam splitter 145*a* either allows the beam 140 to pass through toward lens 155 along the first sample path or reflects the beam 140 toward mirror 148 along the second sample path. Accordingly, the system 100 is configured to direct the beam 140 on either the first sample path or the second sample path by selecting the polarization state of the beam 140 using the polarization switch 136.

Assuming the first sample path is selected using the polarization switch 136, the beam 140 passes through the polarization beam splitter 145*a*, through a polarization beam splitter 145*b*, and further through the lens 155 along an optical axis 143. In an embodiment, the lens 155 directs the beam 140 in a manner such that the beam 140 is a collimating beam with a convergent scanning pattern to scan a retinal area 158 of the sample. The polarization beam splitter 145*b* is configured to pass light having a first polarization state and reflect light have a second polarization state orthogonal to the first polarization state. In accordance with the first sample path, the beam 140 has a polarization state that is configured to pass through the polarization beam splitter 145*b*. Light from the beam 140 that is reflected or backscattered passes back through the first sample path to the interferometer and the photodetector 120.

Assuming the second sample path is selected using the polarization switch 136, the beam 140 is reflected by the polarization beam splitter 145*a* to mirror 148, which in turn reflects the beam 140 through lens 149 to mirror 150. Mirror 150 further reflects the beam 140 to the polarization beam splitter 145*b*. In accordance with the second sample path, the beam 140 has a polarization state such that the polarization beam splitter 145*b* reflects the beam 140 toward lens 155. In an embodiment, the mirrors 148 and 150, the lens 149, and the polarization beam splitter 145*b* are arranged such that the light is passed to a location on the lens 155 that enables the beam 140 to function as a divergent beam with a lateral scanning pattern perpendicular to the sample to enable imaging of an anterior chamber 159 of the eye 156.

Accordingly, both the first sample path and the second sample path of the lens system 147 are arranged to eventually direct the beam 140 onto a common axis 143 so that the beam 140 may scan different depth ranges and/or areas of the same sample (here the eye 156).

Figure 2:
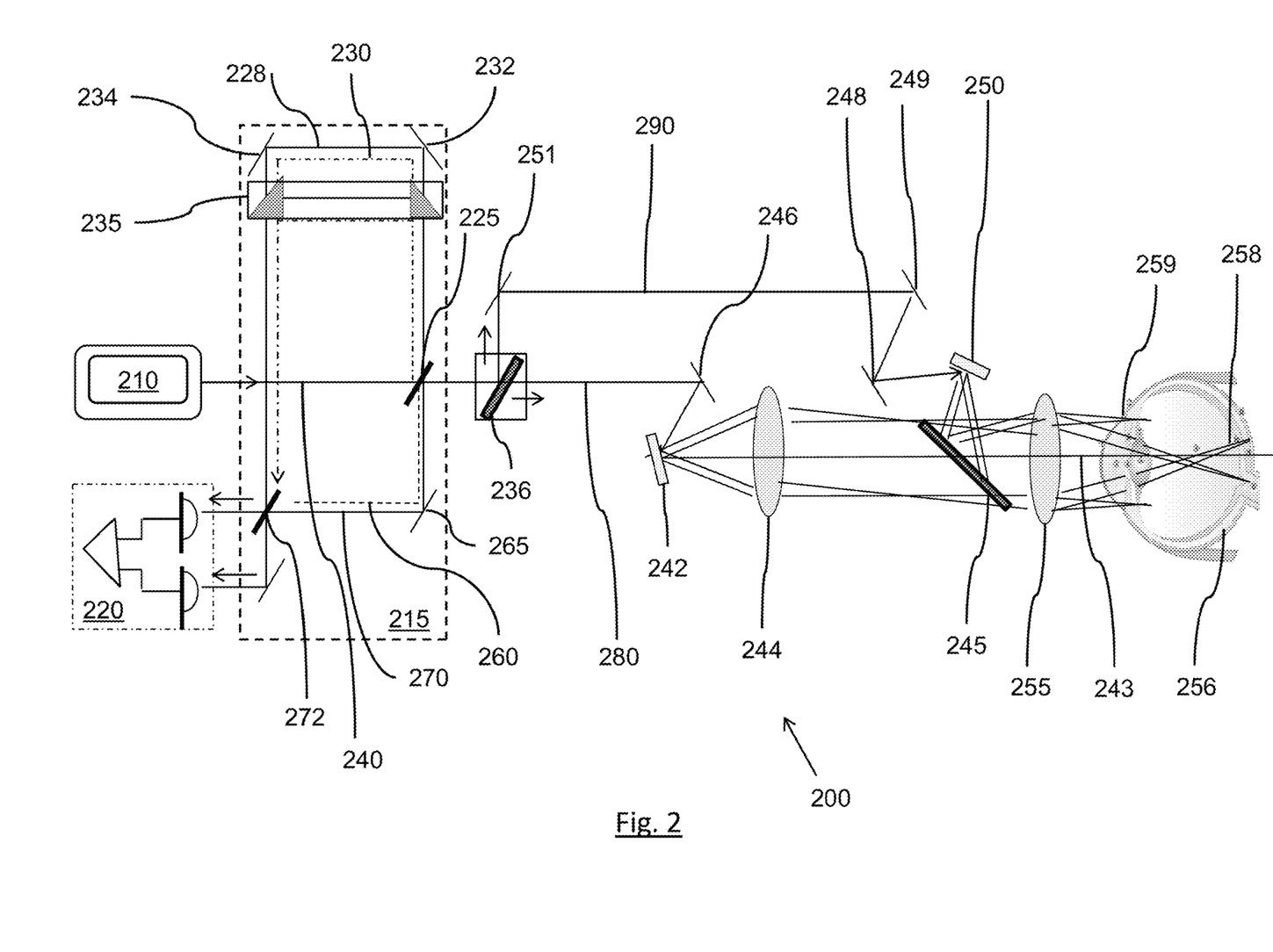
FIG. 2 depicts a representation of an OCT system using a polarization switch in accordance with another illustrative embodiment.

FIG. 2 depicts a representation of an OCT system 200 using a polarization switch in accordance with another illustrative embodiment. In alternative embodiments, fewer, additional, and/or different elements may be present. The OCT system 200 includes a light source 210 that emits a beam 240. The beam 240 is directed into an interferometer 215, which is similar to the configuration of the interferometer 115 of FIG. 1. The interferometer includes a reference path 228 and an interferometer sample path 270. The direction of the reference path 228 in accordance with an embodiment is shown by an arrow 230. The beam 240 from the light source 210 passes through the interferometer 215 to a mirror 225. In an embodiment, the mirror 225 is a half-mirror that reflects some of the light that hits it, but allows other light to pass through. Accordingly, some of the beam 240 is reflected into the reference path 228. The reference path 228 includes two different paths that correspond with a first sample path length for a first sample path 280 and a second sample path length for a second sample path 280. That is, the reference path 228 is capable of changing depending on which part of the sample (e.g., an eye) is being imaged (and subsequently which sample path is being utilized to perform the imaging).

The portion of the beam 240 that passes through the mirror 225 is output from the interferometer 215 and passed to a polarization switch 236. In the embodiment of FIG. 2, the polarization switch 236 is a 1×2 switch that is configured to selectively change the polarization of the light from beam 240. In an embodiment, the polarization switch 236 may be a half-waveplate switch, a liquid crystal switch, or an electro-optics modulator. In additional embodiments, the polarization switch 236 may include any polarization switch known to those of skill in art capable of switching light between two or more orthogonal polarization states.

The polarization switch 236 is configured to switch the polarization of the light from beam 240 between two or more orthogonal polarization states and to direct the light from beam 240 to either the first sample path 280 or the second sample path 290 depending on the polarization state of the beam 240. In other words, if the polarization switch 236 applies a first polarization state to the beam 240, then the beam 240 is directed to the first sample path 280. Alternatively, if the polarization switch 236 applies a second polarization state (which is orthogonal to the first polarization state) to the beam 240, then the beam 240 is directed to the second sample path 290.

The first sample path 280 includes a mirror 246, a scan mirror 242, a lens 244, a polarization beam splitter 245, and a lens 255. The mirror 246 directs the light beam 240 to the scan mirror 242. In an embodiment, the scan mirror 242 is configured to be at a focal point of a lens 244. The scan mirror 242 directs the beam 240 through the lens 244 to the polarization beam splitter 245. Due to the polarization state of the beam 240 the beam 240 passes from the lens 244 through the polarization beam splitter 245. The beam 240 further passes through the lens 255 along an optical axis 243. The first sample path 280 enables use of the beam 240 as a collimating beam with a convergent scanning pattern to scan a retinal area 258 of the sample eye 256. Light from the beam 240 that is reflected or backscattered passes back through the first sample path to the interferometer and the photodetector 220.

The second sample path 290 includes a mirror 251, a mirror 248, a mirror 249, a scan mirror 250, the polarization beam splitter 245, and the lens 255. The mirror 251 directs the light beam 240 from the polarization switch 236 to the mirror 249 which further directs the light beam 240 to the mirror 248, which further directs the light beam 240 to the scan mirror 250. Alternative embodiments may include any number or configuration of mirror to direct the light beam 240 from the polarization switch 236 to the scan mirror 250 as needed. The scan mirror 250 directs the beam 240 to the polarization beam splitter 245. Due to the polarization state of the beam 240, the polarization beam splitter 245 reflects the beam 240 through the lens 255. The second sample path 290 thereby enables use of the beam 240 as a divergent beam with a lateral scanning pattern perpendicular to the sample to enable imaging of an anterior chamber 259 of the eye 256. Light from the beam 240 that is reflected or backscattered passes back through the second sample path to the interferometer and the photodetector 220. The beam splitter 245 is configured direct the beam 240 onto the common axis 243 as that used by the first sample path 280.

Accordingly, both the first sample path 280 and the second sample path 290 of the system 200 are arranged to eventually direct the beam 240 onto the common axis 243 so that the beam 240 may scan different depth ranges and/or areas of the same sample (here the eye 256).

Figure 3:
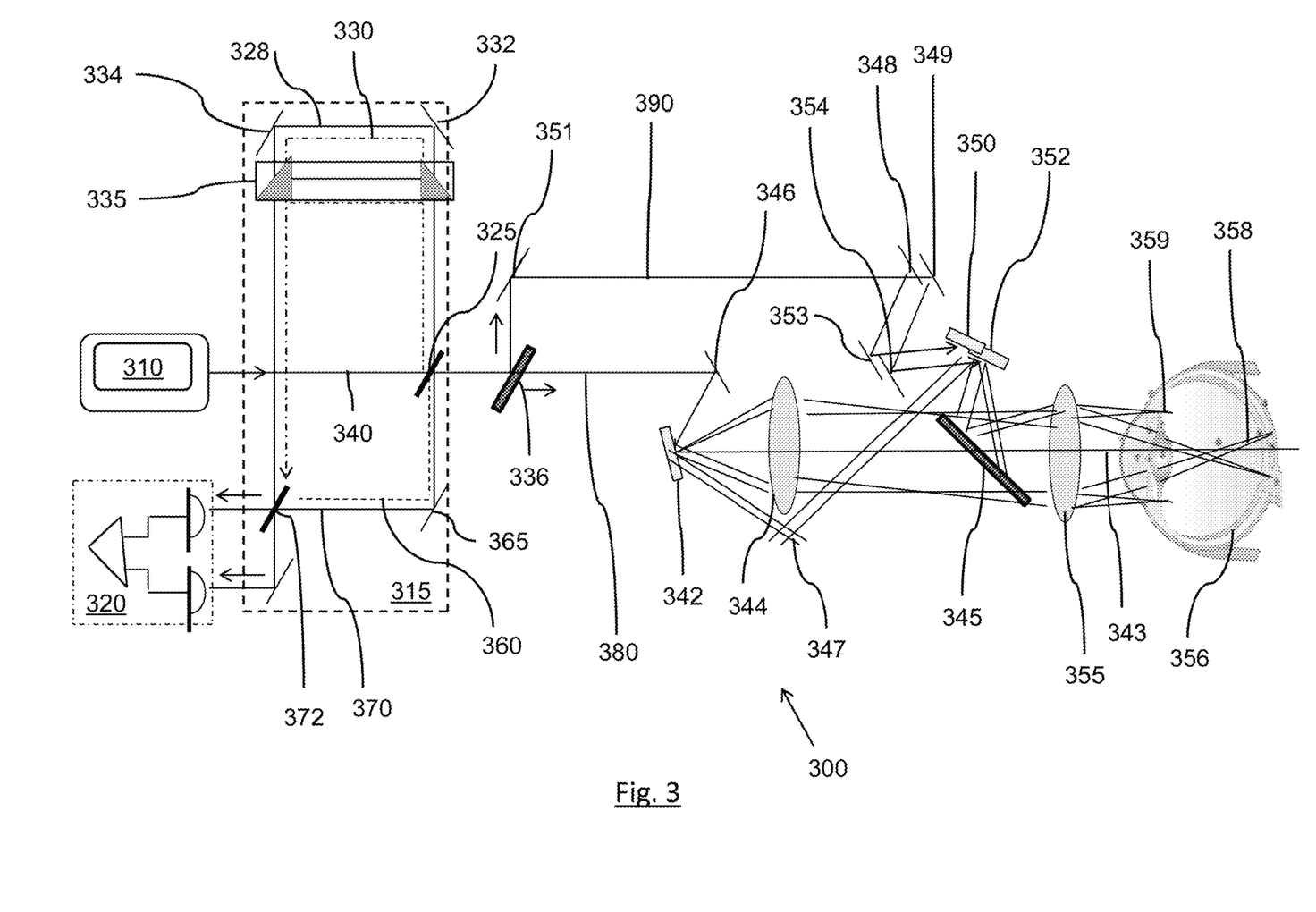
FIG. 3 depicts a representation of an OCT system using a polarization beam splitter in accordance with another illustrative embodiment.

FIG. 3 depicts a representation of an OCT system 300 using a polarization beam splitter 336 and a dump path 347 in accordance with another illustrative embodiment. In alternative embodiments, fewer, additional, and/or different elements may be present. The OCT system 300 includes a light source 310 that emits a beam 340. The beam 340 is directed into an interferometer 315. The interferometer includes a reference path 328 and an interferometer sample path 370.

The direction of the reference path 328 in accordance with an embodiment is shown by an arrow 330. The beam 340 from the light source 310 passes through the interferometer 315 to a mirror 325. The mirror 325 is a half-mirror that reflects some of the light that hits it, but allows other light to pass through. Accordingly, some of the beam 340 is reflected into the reference path 328. The reference path 328 includes two different paths that correspond with a first sample path length for a first sample path 380 and a second sample path length for a second sample path 390. That is, the reference path 328 is capable of changing depending on which part of the sample (e.g., an eye) is being imaged (and subsequently which sample path is being utilized to perform the imaging).

Accordingly, in an example embodiment, when a sample path being utilized with the beam 340 to measure an anterior segment of an eye 356, the reference path 328 is longer, and the light is reflected off of a mirror 332 and a mirror 334. When a different sample path is being utilized to measure a retinal area of the eye 356, a path length switch 335 is activated to shorten the reference path 328, which corresponds to the difference in path length between the first sample path and the second sample path. In an alternative embodiment, the reference path 328 (and the shortened reference path when the path length switch 335 is activated) may be variable in order to provide depth scanning of the eye 356. In an alternative embodiment, instead of having a path length switch 335, the difference in path length between a reference path corresponding to the first sample path and a reference corresponding to the second sample path may be pre-adjusted or predetermined in order to have relative offset/non-offset of depth ranges between the anterior chamber and retinal areas of the eye.

The portion of the beam 340 that passes through the mirror 325 is output from the interferometer 315 and passed to the polarization beam splitter 336. In the embodiment of FIG. 3, the polarization beam splitter 336 is a beam splitter having a wide wavelength band with high polarization isolation. The polarization beam splitter 136 is configured to divide the light from beam 240 into a first sample path 380 having a first polarization state and a second sample path 390 having a second polarization state that is orthogonal to the first polarization state. On the return path, when light from the first sample path 380 and the second sample path 390 have been reflected or backscattered, the polarization beam splitter 336 acts as a combiner. In additional embodiments, the polarization beam splitter 336 may include any beam splitter known to those of skill in art capable of dividing light into beams with two or more orthogonal polarization states.

The first sample path 380 includes a mirror 346, a scan mirror 342, a lens 344, a polarization beam splitter 345, a lens 355, and the dump path 347. The mirror 346 directs light from the first sample path 380 to the scan mirror 342. The scan mirror 342 directs light through the lens 344 to the polarization beam splitter 345. Due to the polarization state of the beam 340 the light passes from the lens 344 through the polarization beam splitter 345. The light further passes through the lens 355. The first sample path 380 enables use of the light as a collimating beam with a convergent scanning pattern to scan a retinal area 358 of the sample eye 356. Light from the beam 340 that is reflected or backscattered passes back through the first sample path to the interferometer and the photodetector 320.

The scan mirror 342 also directs a portion of the light on the first sample path 380 to the dump path 347. The dump path 347 facilitates selectively switching off of the first sample path 380. In an embodiment, both of the first sample path 380 and the second sample path 390 cannot be simultaneously used. When one of the first sample 380 or the second sample path 390 is selected, the other of the sample paths is switched off. To switch off one of the sample paths, the dump path 347 may be used to discard the sample path that has been switched off.

The second sample path 390 includes mirrors 351, 348, 349, 353, and 354, scan mirrors 350 and 352, the polarization beam splitter 345, the lens 355, and the dump path 347. The mirror 351 directs the light from the second sample path 390 from the polarization beam splitter 336 to the mirrors 348 and 349. The mirrors 348 and 349 direct the light to mirrors 353 and 354, respectively. The mirrors 353 and 354 direct the light to the scan mirrors 350 and 352, respectively. Alternative embodiments may include any number or configuration of mirror to direct the light from the polarization beam splitter 336 to the scan mirrors 350 and 352 as needed. The scan mirror 350 directs a portion of the light on the second sample path 390 to the dump path 347.

The scan mirror 3520 directs the remaining light on the second sample path 390 to the polarization beam splitter 345. Due to the polarization state of the light on the second sample path 390, the polarization beam splitter 345 reflects the light through the lens 355. The second sample path 390 thereby enables use of the light as a divergent beam with a lateral scanning pattern perpendicular to the sample to enable imaging of an anterior chamber 359 of the eye 356. Light that is reflected or backscattered passes back through the second sample path 390 to the interferometer and the photodetector 320. The beam splitter 345 is configured to direct the light onto a common axis 343 as that used by the first sample path 380.

Accordingly, both the first sample path 380 and the second sample path 390 of the OCT system 300 are arranged to eventually direct light onto a common axis 343 so that the OCT system 300 may scan different depth ranges and/or areas of the same sample (here the eye 356).

Figure 4:
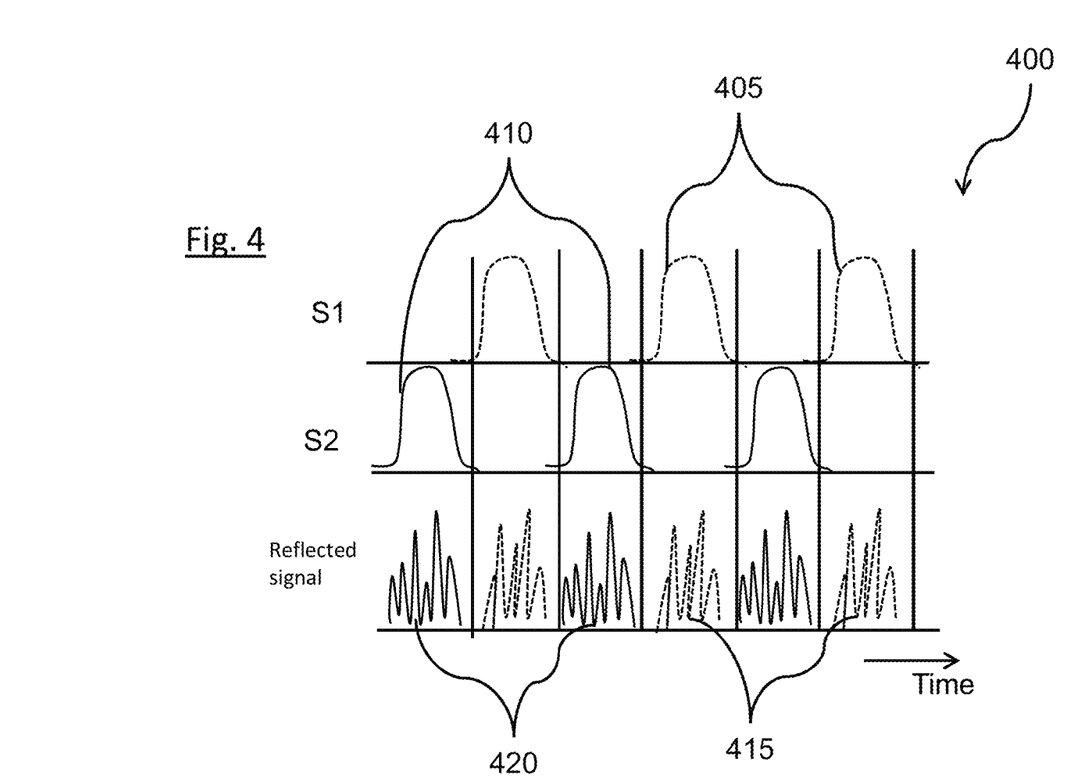
FIG. 4 depicts a graph that demonstrates how light beams having different polarization states are simultaneously and alternately modulated and detected in accordance with an illustrative embodiment.

FIG. 4 depicts a graph 400 that demonstrates how light beams having different polarization states are simultaneously and alternately modulated and detected in accordance with an illustrative embodiment. In alternative embodiments, fewer, additional, and/or different elements may be present. The graph 400 shows a first sample path having light of a first polarization state, for example beams 405. The graph 400 also shows a second sample path having light of a second polarization state that is orthogonal to the first polarization state, for example beams 410. The horizontal axis of the graph 400 is time. Accordingly, the graph 400 demonstrates how a system such as the one demonstrated in FIG. 1 or 2 may be controlled to switch polarization states of a light beam alternately at different times. Accordingly, the polarization states of the light beam are switched orthogonally in sequence.

The first beams 405 of the first sample may yield backscattered or reflected signals 415. The second beams 410 may yield backscattered or reflected signals 420. As an example, the reflected signals 415 may correspond to imaging of an anterior chamber via a first sample path as discussed above with respect to FIG. 1. Similarly, the reflected signals 420 may correspond to imaging of a retinal chamber via a second sample path as discussed above with respect to FIG. 1. The reflected signals 415 and the reflected signals 420 may both be received at a photo-detector, such as the photo-detector 120 shown in FIG. 1 or the photo-detector 220 shown in FIG. 2. In this way, a processing system in communication with the photo-detector can generate a first image and a second image based on the alternating signals 415 and 420 received at the photo-receptor and output to the processing system. For example the two images may be of different image zones or depth ranges of a sample. If the path length difference of the first and second sample paths is pre-adjusted or predetermined and the polarization states of the source light beam are switched quickly, the system can generate real time images of both samples, in one embodiment the anterior chamber and retinal area of the eye 156.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least,"

"greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

What is claimed is:

1. An optical coherence tomography (OCT) system comprising:
   a light source configured to emit a beam;
   an interferometer configured to receive the beam, and further wherein the interferometer comprises:
      a reference path, and
      an interferometer sample path;
   a polarization switch configured to selectively switch a polarization state of the beam between a first polarization state and a second polarization state; and
   a lens system comprising a first sample path and a second sample path,
   wherein the polarization switch is further configured to:
      direct the beam onto the first sample path upon selection of the first polarization state; and
      switch the beam from the first sample path to the second sample path upon selection of the second polarization state that is different from the first polarization state.

2. The OCT system of claim 1, wherein the first polarization state is orthogonal to the second polarization state.

3. The OCT system of claim 1, wherein the light source is a wavelength swept source.

4. The OCT system of claim 1, further comprising a polarization beam splitter configured to route a beam from the first sample path and a beam from the second sample path onto a common axis.

5. The OCT system of claim 1, wherein a beam on the first sample path is configured to image a different image zone or depth range of a sample than a beam on the second sample path.

6. The OCT system of claim 5, wherein the beam on the first sample path is configured to image an anterior chamber of an eye and the beam on the second sample path is configured to image a retina of the eye.

7. The OCT system of claim 5, wherein the first sample path has a divergent beam and a lateral scanning pattern perpendicular to the sample comprising:
   a first lens system, and
   a first scan mirror.

8. The OCT system of claim 7, wherein the second sample path has a collimating beam with a convergent scanning pattern:
   a second lens system, and
   a second scan mirror.

9. The OCT system of claim 1, wherein the lens system comprises a scan mirror configured to direct the beam though a lens to a first polarization beam splitter, wherein the first polarization beam splitter is configured to pass through light of a first polarization state to the first sample path and to reflect light of a second polarization state to the second sample path.

10. The OCT system of claim 9, wherein the lens system further comprises a second polarization beam splitter configured to route a beam from the first sample path and a beam from the second sample path onto a common axis.

11. The OCT system of claim 1, wherein a path length difference between the first sample path and the second sample path is approximately an optical length equivalent to an axial length of a human eye.

12. The OCT system of claim 1, wherein the system comprises only a single scanning mirror.

13. The OCT system of claim 1, wherein the polarization switch comprises a 1×1 polarization switch.

14. The OCT system of claim 1, wherein the polarization switch comprises a 1×2 polarization switch.

15. The OCT system of claim 1, wherein:
   the interferometer comprises a reference path length switch configured to alternate a reference path length between a first reference length and a second reference length;
   the first reference length corresponds to a first sample path length; and
   the second reference length corresponds to a second sample path length.

16. The OCT system of claim 1, further comprising a photo-detector and a processing unit configured to:
   receive, through the photo-detector, a light beam reflected from a sample; and
   generate an image of the sample based on the reflected beam.

17. The OCT system of claim 1, further comprising a scan mirror disposed between the lens system and the polarization switch.

18. The OCT system of claim 1, wherein the polarization switch is an electro-optics modulator or a liquid crystal switch.

* * * * *